(12) United States Patent
Lee et al.

(10) Patent No.: US 11,060,272 B2
(45) Date of Patent: Jul. 13, 2021

(54) URINE-FECES SEPARATION TOILET BOWL AND EXCRETA DISPOSAL SYSTEM USING THE SAME

(71) Applicant: UNIST(ULSAN NATIONAL INSTITUTE OF SCIENCE AND TECHNOLOGY), Ulsan (KR)

(72) Inventors: Hyun Kyung Lee, Ulsan (KR); Jae Weon Cho, Ulsan (KR); Chang Soo Lee, Ulsan (KR); Ja Ai Kim, Ulsan (KR); Mi Jin Choi, Ulsan (KR); Jeong Hyeon Bae, Ulsan (KR)

(73) Assignee: UNIST (ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 182 days.

(21) Appl. No.: 16/345,215

(22) PCT Filed: Jul. 25, 2018

(86) PCT No.: PCT/KR2018/008392
§ 371 (c)(1),
(2) Date: Apr. 25, 2019

(87) PCT Pub. No.: WO2019/107697
PCT Pub. Date: Jun. 6, 2019

(65) Prior Publication Data
US 2020/0299946 A1    Sep. 24, 2020

(30) Foreign Application Priority Data
Nov. 29, 2017 (KR) .......................... 10-2017-0161851

(51) Int. Cl.
*E03D 11/11* (2006.01)

(52) U.S. Cl.
CPC .................................. *E03D 11/11* (2013.01)

(58) Field of Classification Search
CPC ......... E03D 11/11; E03D 11/02; E03D 1/145; E03D 5/014; E03D 5/105; E03D 9/06; E03D 9/032; A47K 13/00
(Continued)

(56) References Cited

U.S. PATENT DOCUMENTS

| | | | |
|---|---|---|---|
| 4,052,758 A * | 10/1977 | Arena | E03D 5/014 4/320 |
| 6,243,887 B1 * | 6/2001 | Palffy | E03F 1/006 4/431 |

(Continued)

FOREIGN PATENT DOCUMENTS

| | | | |
|---|---|---|---|
| EP | 0507687 A1 * | 10/1992 | A47K 13/24 |
| KR | 10-0748849 | 8/2007 | |

(Continued)

OTHER PUBLICATIONS

KR1001990006—English Translation, machine generated Dec. 2020 (Year: 2020).*

(Continued)

*Primary Examiner* — Benjamin R Shaw
(74) *Attorney, Agent, or Firm* — Klarquist Sparkman, LLP

(57) ABSTRACT

Provided is a urine-feces separation toilet bowl including a urine and feces separator configured to separate urine and feces and use them to generate renewable energy. The urine-feces separation toilet bowl includes: a main body portion configured to accommodate excreta; a cover portion having a plate shape, having a first surface and a second surface, and provided on the main body portion, the first surface being arranged towards the inside of the main body portion; a toilet seat portion between the main body portion and the cover portion; an excreta accommodation portion including a first accommodation portion configured to accommodate urine and a second accommodation portion (Continued)

configured to accommodate feces; and an excreta separator between the first accommodation portion and the second accommodation portion and configured to separate the first accommodation portion and the second accommodation portion.

10 Claims, 4 Drawing Sheets

(58) Field of Classification Search
USPC .............................................................. 4/342
See application file for complete search history.

(56) References Cited

U.S. PATENT DOCUMENTS

| | | | | |
|---|---|---|---|---|
| 6,279,176 | B1* | 8/2001 | Aviles ..................... | E03D 1/286 |
| | | | | 4/354 |
| 6,332,229 | B1* | 12/2001 | O'Malley ................ | E03D 5/08 |
| | | | | 4/325 |
| 2012/0144569 | A1* | 6/2012 | Kodat ..................... | E03D 9/005 |
| | | | | 4/222 |
| 2012/0180208 | A1* | 7/2012 | White ..................... | E03D 11/00 |
| | | | | 4/300 |
| 2014/0115764 | A1* | 5/2014 | Cheng ................ | A47K 13/302 |
| | | | | 4/222 |
| 2014/0131595 | A1* | 5/2014 | Nathan ................ | A61L 2/0047 |
| | | | | 250/504 R |
| 2016/0083949 | A1* | 3/2016 | Plas ....................... | E03D 5/105 |
| | | | | 4/420 |
| 2016/0128526 | A1* | 5/2016 | Dobrinsky ........... | A47K 13/302 |
| | | | | 4/233 |
| 2018/0021465 | A1* | 1/2018 | Dobrinsky .............. | E03D 9/052 |
| | | | | 4/233 |
| 2018/0055488 | A1* | 3/2018 | Hall ..................... | G01N 33/493 |
| 2018/0135284 | A1* | 5/2018 | Hurtado Torres ...... | E03D 5/014 |
| 2018/0220858 | A1* | 8/2018 | Onodera ................ | A47K 13/12 |
| 2018/0325336 | A1* | 11/2018 | Chang ..................... | A61L 2/10 |
| 2019/0336629 | A1* | 11/2019 | Dobrinsky ................ | A61L 2/10 |

FOREIGN PATENT DOCUMENTS

| | | |
|---|---|---|
| KR | 10-2008-0098105 | 11/2008 |
| KR | 20-2011-0004837 | 5/2011 |
| KR | 10-1190006 | 10/2012 |
| KR | 10-2014-0048374 | 4/2014 |
| WO | WO-2014003686 A1 * 1/2014 | ............. E03D 5/014 |

OTHER PUBLICATIONS

EP0507687—English Translation, machine generated Dec. 2020 (Year: 2020).*
KR10-2014-0048374—English Translation, machine generated Dec. 2020 (Year: 2020).*
International Search Report and Written Opinion for PCT/KR2018/008392, dated Oct. 23, 2018.
Office Action for Korean Patent Application No. 10-2017-0161851, dated Nov. 21, 2018.

* cited by examiner

URINE-FECES SEPARATION TOILET BOWL AND EXCRETA DISPOSAL SYSTEM USING THE SAME

CROSS REFERENCE TO RELATED APPLICATIONS

This is the U.S. National Stage of International Application No. PCT/KR2018/008392, filed Jul. 25, 2018, which in turn claims the benefit of prior Korean Patent Application No. 10-2017-0161851, filed Nov. 29, 2017. The prior application is incorporated herein in its entirety.

TECHNICAL FIELD

The present disclosure relates to a urine-feces separation toilet bowl and an excreta disposal system using the same, and more particularly, to a urine-feces separation toilet bowl that separates urine and feces and uses them to generate renewable energy, and an excreta disposal system using the toilet bowl.

BACKGROUND ART

Generally, toilet bowls are placed in a space isolated from the outside to allow a user to urinate and defecate, and according to gender, urinals and closet bowls are installed in restrooms for men, and closet bowls are installed in restrooms for women. In this regard, closet bowls installed in existing restrooms collect urine and feces, i.e., excreta, all at once without separation and transfer them to septic tanks which simply only serve to store excreta.

As such, excreta are not recycled in existing restrooms, and it is difficult to recycle excreta since they are in a mixed state. Therefore, to utilize urine and feces as renewable energy resources such as compost or methane gas by separately separating and treating urine and feces, studies have recently been conducted to develop urine-feces separation toilet bowls configured such that urine and feces are separated when urine and/or urine and feces are discharged.

DESCRIPTION OF EMBODIMENTS

Technical Problem

However, in these existing urine-feces separation toilet bowls, excreta are diluted with a large amount of water in a process of washing urine and/or feces discharged by washing water inside a toilet bowl, and thus it is difficult to obtain only a high concentration of excreta, and it is also difficult to utilize the excreta diluted with a large amount of water for renewable energy.

The present disclosure has been made to address various problems including the above-described problems, and it is an object of the present disclosure to provide a toilet bowl including a urine and feces separator configured to separate urine and feces and use them to generate renewable energy. However, this technical problem is provided for illustrative purposes only and is not intended to limit the scope of the present disclosure.

Solution to Problem

According to an aspect of the present disclosure, a urine-feces separation toilet bowl includes a main body portion forming an external appearance and having an opening in an upper portion thereof, the opening allowing excreta to be accommodated in the main body portion; a cover portion having a plate shape, having a first surface and a second surface, and arranged on the main body portion such that the cover portion covers the opening of the main body portion, wherein the first surface is arranged towards the inside of the main body portion and the second surface is provided on a side opposite to that of the first surface; a toilet seat portion arranged between the main body portion and the cover portion such that the toilet seat portion is seated on an edge of the opening; an excreta accommodation portion including a first accommodation portion and a second accommodation portion, wherein the first accommodation portion is provided in a front end of the main body portion and configured to accommodate urine via a first opening, and the second accommodation portion is provided in a rear end of the main body portion and configured to accommodate feces via a second opening; and an excreta separator provided between the first accommodation portion and the second accommodation portion and configured to separate the first accommodation portion and the second accommodation portion.

According to the present embodiment, the urine-feces separation toilet bowl may further include a first washing water supply unit at an upper end of the main body portion and configured to supply washing water for washing at least one of the first accommodation portion and the second accommodation portion.

According to the present embodiment, the urine-feces separation toilet bowl may further include a second washing water supply unit at the front end of the main body portion and configured to supply washing water only to the first accommodation portion.

According to the present embodiment, the second washing water supply unit may include a second washing water supply hole through which washing water is supplied, wherein the second washing water supply hole is positioned higher than the first opening.

According to the present embodiment, the urine-feces separation toilet bowl may further include a feces discharge hole connected to the second accommodation portion and extending towards a side opposite to that of the first accommodation portion.

According to the present embodiment, the urine-feces separation toilet bowl may further include a vacuum pump connected to the feces discharge hole and configured to discharge to the outside, by vacuum and via the feces discharge hole, feces which have been discharged into the second accommodation portion.

According to the present embodiment, the urine-feces separation toilet bowl may further include a feces collector connected to the feces discharge hole and configured to collect feces discharged to the outside of the main body portion via the feces discharge hole.

According to the present embodiment, the urine-feces separation toilet bowl may further include a sterilization processor at the first surface of the cover portion and configured to sterilize an inside of the main body portion.

According to the present embodiment, the cover portion includes a translucent plate configured to block ultraviolet rays emitted from the inside of the main body portion in a central portion of the cover portion, and the sterilization processor is arranged along an edge of the translucent plate.

According to the present embodiment, the sterilization processor may include an ultraviolet lamp, wherein the ultraviolet lamp is turned on when the cover portion is closed, and turned off when the cover portion is opened.

According to the present embodiment, sealing water may be present in the second accommodation portion in an amount of 500 ml or less.

According to another aspect of the present disclosure, an excreta disposal system includes: a urine-feces separation toilet bowl including: a main body portion forming an external appearance and having an opening in an upper portion thereof, the opening allowing excreta to be accommodated in the main body portion, an excreta accommodation portion including a first accommodation portion and a second accommodation portion, wherein the first accommodation portion is provided in a front end of the main body portion and configured to accommodate urine via a first opening, and the second accommodation portion is provided in a rear end of the main body portion and configured to accommodate feces via a second opening; and an excreta separator between the first accommodation portion and the second accommodation portion and configured to separate the first accommodation portion and the second accommodation portion; a feces collector connected to the first accommodation portion and configured to collect feces ejected into the first accommodation portion; and a resource generation unit configured to process the feces collected in the feces collector to be regenerated as a resource.

According to the present embodiment, the feces collector may further include a vacuum pump configured to discharge to the outside, by vacuum and via a feces discharge hole, the feces ejected into the first accommodation portion.

According to the present embodiment, the urine-feces separation toilet bowl may further include a washing water supply unit at an upper end of the main body portion and configured to supply washing water for washing at least one of the first accommodation portion and the second accommodation portion, wherein the washing water supply unit is configured to supply washing water after feces is collected in the feces collector by the vacuum pump and wash at least one of the first accommodation portion and the second accommodation portion.

According to the present embodiment, a ratio of the washing water to the feces accommodated in the feces collector may be in a range of 2:1 to 3:1.

Other aspects, features, and advantages will become apparent from the following drawings, claims, and detailed description of the present disclosure.

Advantageous Effects of Disclosure

As is apparent from the foregoing description, according to an embodiment of the present disclosure, a toilet bowl including a urine and feces separator configured to separate urine and feces and use them to generate renewable energy. In addition, these effects are not intended to limit the scope of the present disclosure.

MODE OF DISCLOSURE

Figure 1:
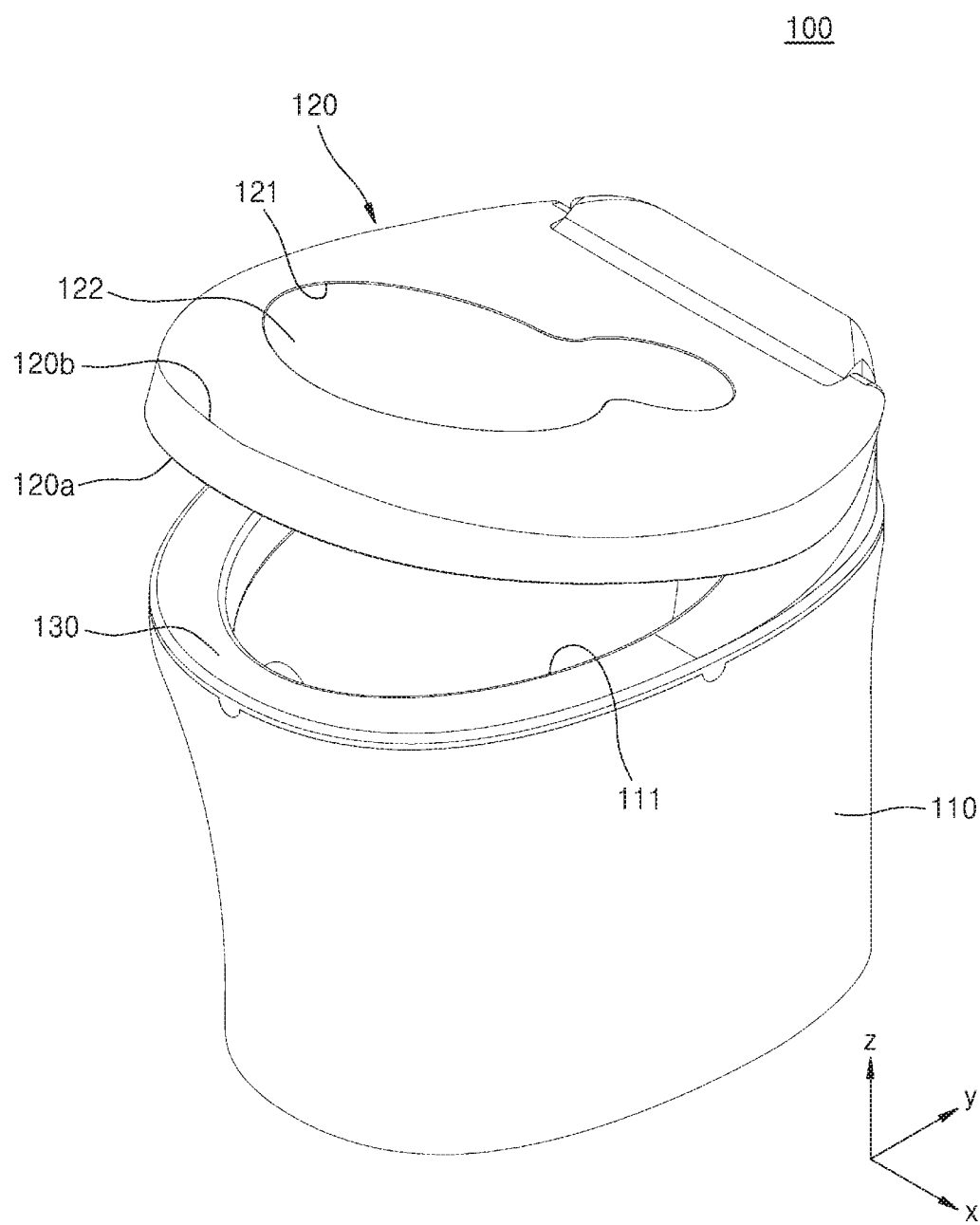
FIG. 1 is a schematic perspective view of a urine-feces separation toilet bowl according to an embodiment of the present disclosure.

Various modifications may be made to the present disclosure and the present disclosure may have various embodiments, and thus specific embodiments will be described in detail in the detailed description with reference to the accompanying drawings. Effects and features of the present disclosure and methods of achieving them will become apparent with reference to the embodiments described below as well as the drawings. However, the present disclosure is not limited to the embodiments set forth herein, but may be embodied in many different forms.

Hereinafter, embodiments of the present disclosure will be described in detail with reference to the accompanying drawings, like reference numerals denote like or corresponding components throughout the drawings, and a detailed description thereof will be provided once.

In the following embodiments, the terms 'first', 'second', and the like are used to distinguish one element from another element, not for the purposes of limitation. In addition, the singular forms are intended to include the plural forms unless the context clearly indicates otherwise.

Meanwhile, the term 'including', 'having', or the like is intended to specify the presence of stated features or components, but does not preclude the addition of one or more other features or components. In addition, when a portion of a film, a region, a component, or the like is referred to as being "above" or "on" another portion, it includes not only a case in which the portion is "directly above" or "directly on" another portion, but also a case in which another film, another region, another component, or the like is present therebetween.

In the drawings, the sizes of components may be exaggerated or reduced for convenience of explanation. For example, the size and thickness of each component illustrated in the drawings are arbitrarily shown for convenience of explanation, and thus the present disclosure is not particularly limited thereto.

X-, y-, and z-axes are not limited to three axes on the orthogonal coordinate system, and may be interpreted in a broad sense including these. For example, the x-axis, y-axis, and z-axis may be perpendicular to each other, but may also refer to different directions that are not perpendicular to each other.

When an embodiment is implemented in a different way, a certain process may be performed in an order opposite to the described order. For example, two consecutively described processes may be performed substantially at the same time, or may be performed in an order opposite to the described order.

FIG. 1 is a schematic perspective view of a urine-feces separation toilet bowl 100 according to an embodiment of the present disclosure.

Referring to FIG. 1, the urine-faces separation toilet bowl 100 according to an embodiment of the present disclosure includes a main body portion 110, a cover portion 120 on the main body portion 110, and a toilet seat portion 130 between the main body portion 110 and the cover portion 120. The main body portion 110 may form an external appearance and have an opening 111 in an upper portion thereof so that excreta may be accommodated therein. A user may eject excreta into the main body portion 110 via the opening 111 formed in the upper portion of the main body portion 110. As will be described below, the main body portion 110 may include an excreta accommodation portion 140 capable of accommodating excreta therein, and the excreta accommodation portion 140 may separate and accommodate feces and urine.

The cover portion 120 may have a plate shape and may be provided on the main body portion 110 so as to cover the opening 111 of the main body portion 110. The cover portion 120 may have a first surface 120a and a second surface 120b provided on the opposite side of the first surface 120a, the first surface 120a may be arranged towards the inside of the main body portion 110, and the second surface 120b may be arranged towards the outside of the second surface 120b. The cover portion 120 may be slightly bigger than the opening 111 of the main body portion 110.

The toilet seat portion 130 may be provided between the cover portion 120 and the main body portion 110, and the toilet seat portion 130 may have a form with a central opening that corresponds to the opening 111 of the main body portion 110 and may have a shape corresponding to that of an existing toilet seat. In some cases, the cover portion 120 and the main body portion 110 may be integrally formed, and a configuration such as a bidet may be additionally installed.

The cover portion 120 may have an opening 121 in a central portion thereof, and the opening 121 may be sealed by a translucent plate 122 so as to form a window-like structure. In the present embodiment, the plate 122 may be made of a transparent or translucent plastic material. In addition, the translucent plate 122 may be a translucent plate that shields ultraviolet rays emitted from the inside of the main body portion 110. That is, a translucent plate may be defined as a plate that blocks ultraviolet light, but through which visible light, infrared light, and the like pass. In this way, when viewed with the naked eye, harmful ultraviolet rays may be blocked and the presence or absence of a user's excreta remaining in the toilet bowl may be indirectly confirmed.

For example, in the case of a restroom used by many people, when a toilet bowl is closed by a cover, it cannot be confirmed whether excreta remains inside the toilet bowl or is completely removed, and to check this, a user has to open the toilet bowl. At this time, when a user's excreta remains inside the toilet bowl, it is not hygienic and it makes the next user to feel very unpleasant. Therefore, the urine-faces separation toilet bowl 100 according to the present disclosure includes a hole in a central portion of the cover portion 120 to allow a user to identify the inside of the main body portion 110 and the transparent plate 122 configured to seal the hole, and thus it is possible to identify a state of the inside of the main body portion 110 even in a state in which the toilet bowl 100 is covered by the cover portion 120.

Figure 3:
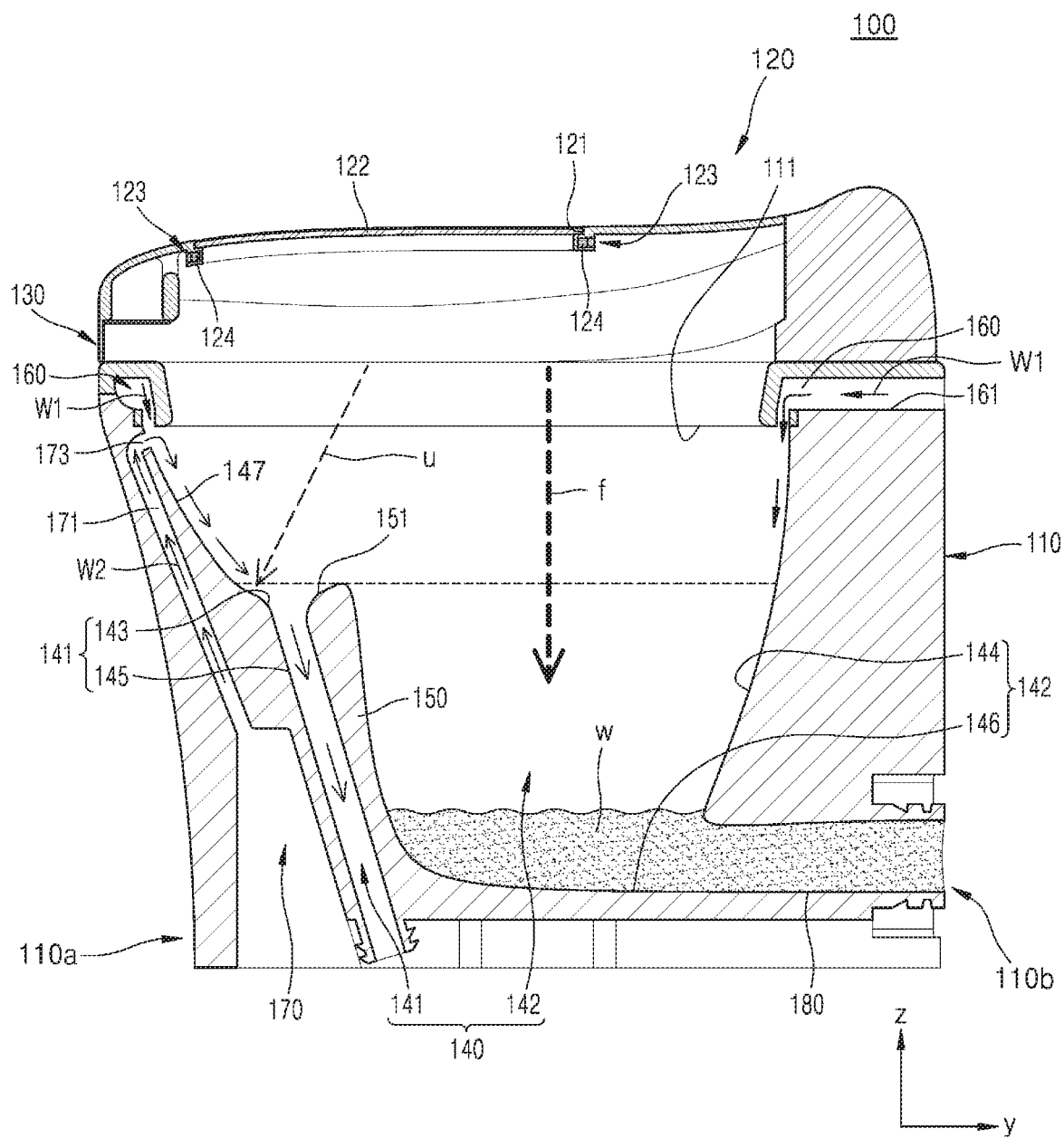
FIG. 3 is a schematic cross-sectional view of the urine-feces separation toilet bowl of FIG. 1.

Meanwhile, referring to FIG. 3, a sterilization processor 123 may be provided at the first surface 120a of the cover portion 120 to sterilize the inside of the main body portion 110. The sterilization processor 123 may be provided along an edge of the opening 121 of the cover portion 120. The sterilization processor 123 may include an ultraviolet lamp, and the ultraviolet lamp may be controlled to be turned on when the cover portion 120 is closed and to be turned off when the cover portion 120 is opened.

Figure 2:
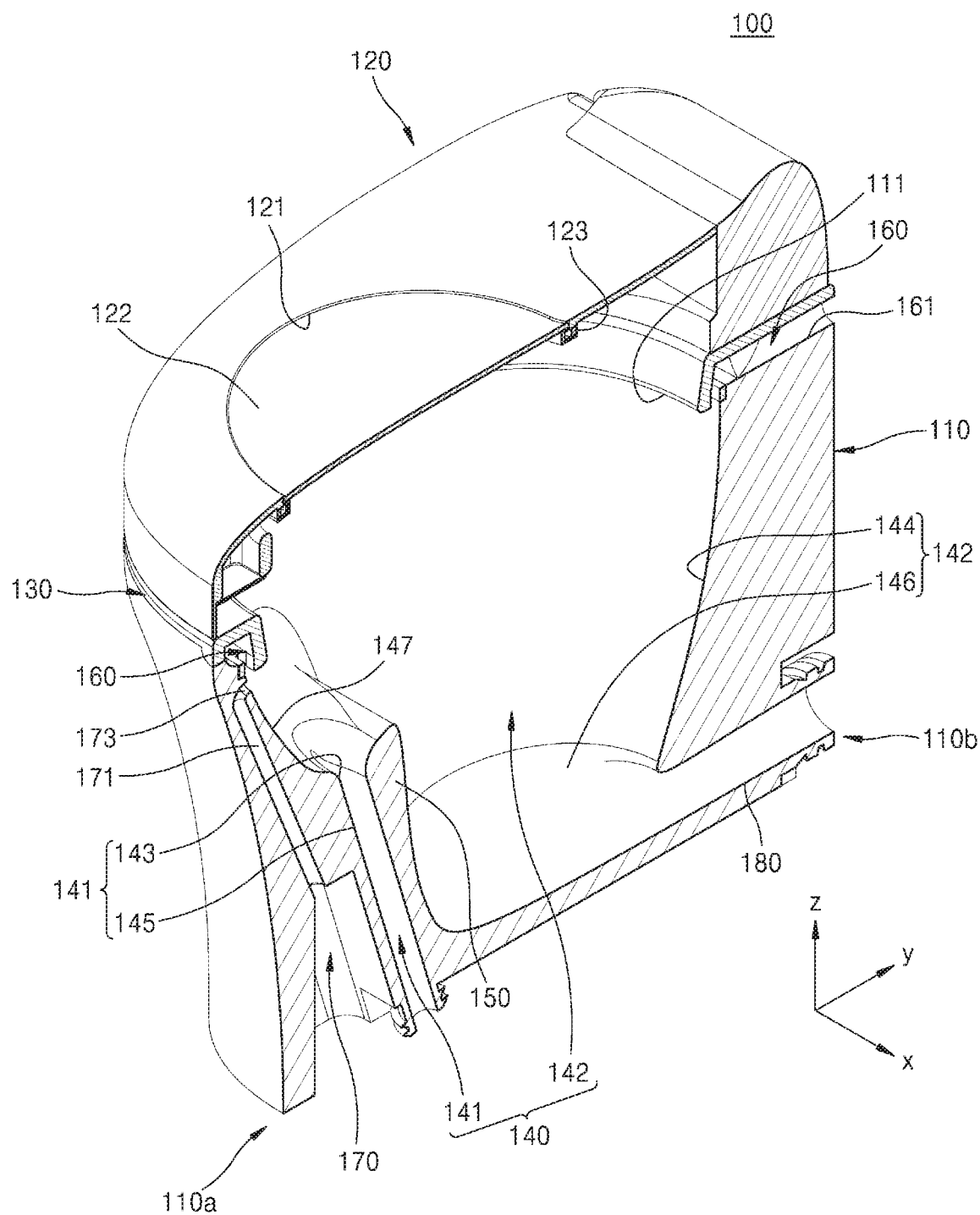
FIG. 2 is a schematic perspective cross-sectional view of the urine-feces separation toilet bowl of FIG. 1.

FIG. 2 is a schematic perspective cross-sectional view of the urine-faces separation toilet bowl 100 of FIG. 1. FIG. 2 illustrates a state in which the cover portion 120 of the toilet bowl 100 is closed.

Referring to FIGS. 1 and 2, the urine-faces separation toilet bowl 100 according to an embodiment of the present disclosure includes the excreta accommodation portion 140 configured to accommodate urine and/or feces inside the main body portion 110. The excreta accommodation portion 140 may include a first accommodation portion 141 provided in a front end 110a of the main body portion 110 and configured to accommodate urine, and a second accommodation portion 142 provided in a rear end 110b of the main body portion 110 and configured to accommodate feces. In this regard, the front end 110a of the main body portion 110 may be construed as meaning a front view when a user is seated on the toilet seat portion 130, and the rear end 110b of the main body portion 110 may be understood as a portion located on the side opposite to that of the front end 110a.

The first accommodation portion 141 may accommodate urine therein via a first opening 143, and the second accommodation portion 142 may accommodate feces therein via a second opening 144. As described above, the first accommodation portion 141 is located in the front end 110a of the main body portion 110, and the second accommodation portion 142 is located in the rear end 110b of the main body portion 110, and these arrangements are related to a body structure of a user. That is, when a user is seated on the toilet seat portion 130, urine is ejected by pressure towards the front end 110a of the main body portion 110, whereas feces is ejected through gravity towards a bottom surface 146. Therefore, in the urine-faces separation toilet bowl 100 according to an embodiment of the present disclosure, to separate urine and feces, the first accommodation portion 141 configured to accommodate urine is arranged in the front end 110a of the main body portion 110, and the second accommodation unit 142 configured to accommodate feces is arranged in the rear end 110b of the main body portion 110.

The first opening 143 of the first accommodation portion 141 may be smaller than the second opening 144 of the second accommodation portion 142. Such a configuration is because the first accommodation portion 141 accommodates urine in a liquid phase, while the second accommodation portion 142 accommodate feces in a solid phase, and thus the second opening 144 may be bigger than the first opening 143. For the same reason, the second accommodation portion 142 may also be larger than the first accommodation portion 141.

The first accommodation portion 141 may include a urine discharge channel 145, and the urine discharge channel 145 may be arranged to be inclined with respect to the ground. Urine may be smoothly discharged to the outside via the urine discharge channel 145 arranged to be inclined with respect to the ground. The second accommodation portion 142 may include the bottom surface 146, and feces ejected into the second accommodation portion 142 may be seated on the bottom surface 146.

Meanwhile, an excreta separator 150 may be provided between the first accommodation portion 141 and the second accommodation portion 142, and the first accommodation portion 141 and the second accommodation portion 14 may be defined by the excreta separator 150. With respect to the excreta separator 150, the first accommodation portion 141 may be located in the front end 110a of the main body portion 110, and the second accommodation portion 142 may be located in the rear end 110b of the main body portion 110. The excreta separator 150 may have a height corresponding to about ⅔ of an internal depth of the main body portion 110, but the present disclosure is not particularly limited thereto.

Meanwhile, washing water supply units 160 and 170 may be arranged at an upper end of the main body portion 110 to supply washing water for washing the excreta accommodation portion 140 inside the main body portion 110. The washing water supply units 160 and 170 may include a first washing water supply unit 160 configured to wash the excreta accommodation portion 140 and a second washing water supply unit 170 configured to supply washing water only to the first accommodation portion 141 that accommodates urine. The first and second washing water supply units 160 and 170 may be connected to a public water pipe (not shown), and a user may manipulate a valve (not shown) or button (not shown) for controlling the public water pipe to be opened or closed, thereby supplying washing water to the excreta accommodation portion 140.

The first washing water supply unit 160 may supply washing water for washing at least one of the first accommodation portion 141 and the second accommodation portion 142. That is, the first washing water supply unit 160 may supply washing water to at least one of the first accommodation portion 141 and the second accommodation portion 142 when feces or urine and feces is/are discharged by a user.

As illustrated in FIGS. 2 and 3, the first washing water supply unit 160 may supply washing water via a first washing water supply path 161 extending from the rear end 110b, and the washing water may flow along the periphery of the opening 111 of the main body portion 110 onto an inner wall of the main body portion 110 and flow into the excreta accommodation portion 140. In this case, the washing water flowing into the excreta accommodation portion 140 may be completely discharged to the outside of the main body portion 110 without remaining inside the main body portion 110.

The second washing water supply unit 170 may be located in the front end 110a of the main body portion 110 and may supply washing water only to the first accommodation portion 141. The second washing water supply unit 170 may include a second washing water supply path 171 configured to supply washing water and a second washing water supply hole 173 through which the washing water is directly ejected. As illustrated in FIGS. 2 and 3, the second washing water supply hole 173 may be located at a lower height from the ground than the first washing water supply unit 160. In addition, the second washing water supply hole 173 may be positioned higher than the first opening 143 of the first accommodation portion 141. Therefore, the washing water discharged from the second washing water supply unit 170 may be completely supplied to the first accommodation portion 141. Since there is no need to completely wash the excreta accommodation portion 140 when a user only urinates, only the first accommodation portion 141 configured to accommodate urine may be washed by operating only the second washing water supply unit 170. Accordingly, the toilet bowl may be cleaned with only 30% or less of washing water as compared to when the excreta accommodation portion 140 is completely washed, and thus water may be saved, which is economical.

In addition, the urine-faces separation toilet bowl 100 according to an embodiment of the present disclosure may further include a feces discharge hole 180 connected to the second accommodation portion 142 and extending towards the rear end 110b of the main body portion 110. The feces discharge hole 180 may be connected to a feces discharge pipe (not shown) to store feces in a feces collector 200 (see FIG. 4) located outside of the toilet bowl 100. Referring to FIGS. 2 and 3, the feces discharge hole 180 may extend in parallel to the bottom surface 146 of the second accommodation portion 142, but the present disclosure is not particularly limited thereto.

As illustrated in FIG. 3, a small amount of sealing water w may be present on the bottom surface 146 of the second accommodation portion 142. The small amount of sealing water w may be held in the second accommodation portion 142 even when a user is not using the toilet bowl. In the present embodiment, the amount of sealing water w present in the second accommodation portion 142 may be 500 ml or less. The feces discharge hole 180 may be connected to a vacuum pump 400 (see FIG. 4) so that feces discharged into the second accommodation portion 142 may be discharged by vacuum to the outside via the feces discharge hole 180. The feces discharged to the outside may be stored in the feces collector 200 connected to the feces discharge hole 180. The feces collector 200 may be, for example, an intermediate storage tank, or may be a separate storage unit configured to store feces for recycling. The feces stored in the feces collector 200 may be recycled as methane gas through anaerobic microorganisms or the like.

As such, the urine-faces separation toilet bowl 100 according to an embodiment of the present disclosure includes a system significantly different from existing toilet bowls in that a toilet bowl is filled with a large amount of sealing water and excreta is removed along with a large amount of sealing water without separation of urine and feces.

That is, in the urine-faces separation toilet bowl 100 according to an embodiment of the present disclosure, a minute amount of sealing water w is present, and discharged feces may be discharged to the outside of the toilet bowl 100 along with the minute amount of sealing water w. When urine and feces are discharged, about 9 L of water is used in existing general toilet bowls, and about 6 L of water is used in existing water-saving toilet bowls. In contrast, in the present embodiment, the amount of sealing water w discharged together with feces is about 500 ml or less, which is very small, i.e., about $1/15$ to about $1/10$ of that used in general toilet bowls. The collected feces may be used to obtain renewable energy such as methane gas or the like using anaerobic microorganisms or the like.

In addition, a small amount of diluted sealing water w may pass through the feces collector 200 and may be used in a process of decomposing an organic material by anaerobic microorganisms in a resource regeneration unit 210, thereby enhancing methane production efficiency. Experimental results show that when an excessive quantity of water is used for dilution and overflows in this process or water-free excreta is used in a dried state, a methane yield is rather decreased. Thus, the methane yield may be increased by using a minimum amount of sealing water w needed to efficiently obtain methane, and feces may be easily discharged to the outside of the toilet bowl 100.

In the related art, many techniques for obtaining renewable energy using human excreta have been proposed. However, existing collected excreta is diluted by mixing with sealing water and washing water, and thus it is difficult to obtain pure excreta, and as such, there is a problem in that the efficiency of utilizing excreta diluted with water for renewable energy is significantly reduced. In addition, it is more efficient to utilize feces than urine in generating renewable energy such as methane gas or the like, but existing toilet bowls discharge a mixture of urine and feces, and thus it is difficult to obtain only pure feces. Therefore, in the urine-faces separation toilet bowl 100 according to an embodiment of the present disclosure, feces and urine may be collected after separation, and the discharged feces may be directly collected without using water, thereby obtaining and utilizing only pure feces. In addition, the environment of a restroom may be kept pleasant since there is no remaining sealing water in the toilet bowl 100, and the inside of the toilet bowl 100 may be washed by separating urine and feces, and thus water may be efficiently saved.

FIG. 3 is a schematic cross-sectional view of the urine-faces separation toilet bowl 100 of FIG. 1.

Referring to FIG. 3, as described above, user's urine is accommodated in the first accommodation portion 141, and user's feces are accommodated in the second accommodation portion 142. In view of the body structure of humans, urine is discharged towards the front end 110*a* of the main body portion 110, and feces are discharged towards the rear end 110*b* of the main body portion 110. As illustrated in FIG. 3, urine is discharged towards a urine discharge surface 147 along a first direction u. The urine discharge surface 147 may be inclined with respect to the ground similar to the urine discharge channel 145 of the first accommodation portion 141, and urine flows into the first accommodation portion 141 along the urine discharge surface 147. In this regard, a jaw portion 151 may be formed at an upper portion of the excreta separator 150 to prevent urine from overflowing to the second accommodation portion 142.

When urine is accommodated in the first accommodation portion 141 and is discharged to the outside along the urine discharge channel 145, the second washing water supply unit 170 may be operated. The second washing water supply unit 170 may be connected to a public water pipe (not shown), and a user may manipulate a valve (not shown) or button (not shown) for controlling the public water pipe to be opened or closed, thereby supplying washing water to the first accommodation portion 141.

Washing water of the second washing water supply unit 170 is supplied to the second washing water supply hole 173 via the second washing water supply path 171. The washing water discharged via the second washing water supply hole 173 washes the urine discharge surface 147, and then flows into the first accommodation portion 141 to wash the first accommodation portion 141. The washing water supplied via the second washing water supply unit 170 completely flows into the first accommodation portion 141 and is not supplied to the second accommodation portion 142. Since there is no need to completely wash the excreta accommodation portion 140 including the second accommodation portion 142 when a user only urinates, only the first accommodation portion 141 configured to accommodate urine may be washed by operating only the second washing water supply unit 170. Accordingly, the toilet bowl 100 may be cleaned with only 30% or less of washing water as compared to the case in which the excreta accommodation portion 140 is completely washed, and thus a water saving effect is obtained, which is economical.

Feces may be discharged towards the bottom surface 146 of the second accommodation portion 142 in a second direction f. The bottom surface 146 of the second accommodation portion 142 may be substantially parallel to the ground, and feces may be discharged to the outside of the toilet bowl 100 via the feces discharge hole 180 extending towards the rear end 110*b* of the main body portion 110. Although not shown in FIG. 3, feces discharged into the second accommodation portion 142 may be stored in the feces collector 200 located outside of the toilet bowl 100 by the vacuum pump 400 connected to the feces discharge hole 180. That is, in the urine-faces separation toilet bowl 100 according to an embodiment of the present disclosure, the feces discharged into the second accommodation portion 142 may be directly collected through the vacuum pump 400 without using water.

As such, once feces are discharged to the outside of the toilet bowl 100, the first washing water supply unit 160 may be operated. The washing water of the first washing water supply unit 160 is not supplied to discharge feces to the outside of the toilet bowl 100, but may serve to clean the second accommodation portion 142 after feces is discharged to the outside of the toilet bowl 100.

Although the urine-faces separation toilet bowl 100 has been mainly described, the present disclosure is not limited thereto. For example, a system for processing collected excreta using the urine-faces separation toilet bowl 100 is construed as being within the scope of the present disclosure.

Figure 4:
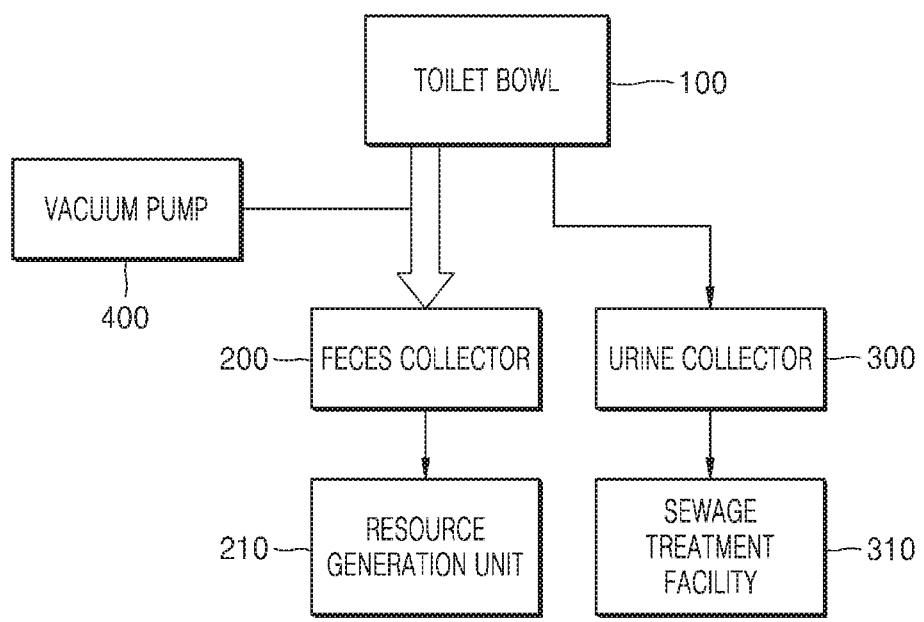
FIG. 4 is a schematic block diagram illustrating an excreta disposal system according to an embodiment of the present disclosure.

FIG. 4 is a schematic block diagram illustrating an excreta disposal system according to an embodiment of the present disclosure.

Referring to FIG. 4, the excreta disposal system according to an embodiment of the present disclosure may use feces collected using the above-described urine-faces separation toilet bowl 100. As described above, in the urine-faces separation toilet bowl 100 according to an embodiment of the present disclosure, discharged feces itself may be discharged to the outside of the toilet bowl 100 by vacuum, thereby obtaining only pure feces that is not diluted with water. The feces discharged to the outside of the toilet bowl 100 may be stored in the feces collector 200. The feces collector 200 may be, for example, a septic tank or a separate storage tank for recycling.

The feces stored in the feces collector 200 may be recycled as energy in the resource regeneration unit 210. In one embodiment, the feces collector 200 and the resource regeneration unit 210 may be provided separately or integrally. Unlike a urine collector 300, which will be described below, the feces collector 200 is characterized in that it stores only pure feces that is not mixed with washing water. The collected feces may be used to obtain renewable energy such as methane gas or the like using anaerobic microorganisms or the like.

Meanwhile, urine is collected in the first accommodation portion 141 and discharged to the outside of the toilet bowl 100, and the discharged urine may be collected in the urine collector 300. The urine collector 300 may be, for example, an intermediate storage tank such as a septic tank. In this regard, unlike the feces collector 200 configured to collect only pure feces, the urine collector 300 may simultaneously store urine and washing water.

In one embodiment, the urine collector 300 may perform predetermined treatment on urine and washing water, thereby sorting them into wastewater and sludge, and the sorted wastewater may be discharged to a wastewater reuse system (not shown) through purification and the sludge may be discharged to a sewage treatment facility 310. In other embodiments, the urine collected in the urine collector 300 may also be utilized for renewable energy. The urine collected in the urine collector 300 may be used to produce fertilizer by separating phosphorus (P) or may be mixed with anaerobic microorganisms to increase the methane yield.

In the related art, many techniques for obtaining renewable energy using human excreta have been proposed. However, existing collected excreta is diluted by being mixed with sealing water and washing water, and thus it is difficult to obtain pure excreta, and as such, there is a problem in that the efficiency of utilizing excreta diluted with water for renewable energy is significantly reduced. In addition, it is more efficient to utilize feces than urine in generating renewable energy such as methane gas or the like, but existing toilet bowls discharge a mixture of urine and feces, and thus it is difficult to obtain only pure feces. Therefore, in the urine-faces separation toilet bowl 100 according to an embodiment of the present disclosure, feces and urine may be collected after separation, and the discharged feces may be directly collected without using water, thereby obtaining and utilizing only pure feces. In addition, the environment of a restroom may be kept pleasant since there is no remaining sealing water in the toilet bowl 100, and the inside of the toilet bowl 100 may be washed by separating urine and feces, and thus water may be efficiently saved.

While the present disclosure has been described with reference to embodiments illustrated in the drawings, it is to be understood by those of ordinary skill in the art that various modifications and other embodiments equivalent thereto may be made therefrom. Therefore, the true scope of the present disclosure should be defined by the technical spirit of the appended claims.

The invention claimed is:

1. A urine-feces separation toilet bowl comprising:
   a main body portion forming an external appearance and having an opening in an upper portion thereof, the opening allowing excreta to be accommodated in the main body portion;
   a cover portion having a plate shape, having a first surface and a second surface, and arranged on the main body portion such that the cover portion covers the opening of the main body portion, wherein the first surface is arranged towards the inside of the main body portion and the second surface is provided on a side opposite to that of the first surface;
   a toilet seat portion arranged between the main body portion and the cover portion such that the toilet seat portion is seated on an edge of the opening;
   an excreta accommodation portion comprising a first accommodation portion and a second accommodation portion, wherein the first accommodation portion is provided in a front end of the main body portion and configured to accommodate urine via a first opening, and the second accommodation portion is provided in a rear end of the main body portion and configured to accommodate feces via a second opening, and
   an excreta separator provided between the first accommodation portion and the second accommodation portion and configured to separate the first accommodation portion and the second accommodation portion,
   wherein the cover portion comprises a translucent plate configured to block ultraviolet rays emitted from the inside of the main body portion in a central portion of the cover portion, and a sterilization processor is arranged along an edge of the translucent plate.

2. The urine-feces separation toilet bowl of claim 1, further comprising a first washing water supply unit at an upper end of the main body portion and configured to supply washing water for washing at least one of the first accommodation portion and the second accommodation portion.

3. The urine-feces separation toilet bowl of claim 1, further comprising a second washing water supply unit at the front end of the main body portion and configured to supply washing water to the first accommodation portion.

4. The urine-feces separation toilet bowl of claim 3, wherein the second washing water supply unit comprises a second washing water supply hole through which washing water is supplied, wherein the second washing water supply hole is positioned higher than the first opening.

5. The urine-feces separation toilet bowl of claim 1, further comprising a feces discharge hole connected to the second accommodation portion and extending towards a side opposite to that of the first accommodation portion.

6. The urine-feces separation toilet bowl of claim 5, further comprising a vacuum pump connected to the feces discharge hole and configured to discharge to the outside, by vacuum and via the feces discharge hole, feces which have been discharged into the second accommodation portion.

7. The urine-feces separation toilet bowl of claim 5, further comprising a feces collector connected to the feces discharge hole and configured to collect feces discharged to the outside of the main body portion via the feces discharge hole.

8. The urine-feces separation toilet of claim 1, wherein the sterilization processor is at the first surface of the cover portion and configured to sterilize an inside of the main body portion.

9. The urine-feces separation toilet bowl of claim 8, wherein the sterilization processor comprises an ultraviolet lamp, wherein the ultraviolet lamp is turned on when the cover portion is closed, and turned off when the cover portion is opened.

10. The urine-feces separation toilet bowl of claim 1, wherein sealing water is present in the second accommodation portion in an amount of 500 ml or less.

* * * * *